US008961763B2

(12) United States Patent
Dunbar et al.

(10) Patent No.: US 8,961,763 B2
(45) Date of Patent: Feb. 24, 2015

(54) DUAL-PORE DEVICE

(75) Inventors: William Dunbar, Santa Cruz, CA (US); Jungsuk Kim, Santa Cruz, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 13/882,191

(22) PCT Filed: Jul. 18, 2012

(86) PCT No.: PCT/US2012/047107
§ 371 (c)(1),
(2), (4) Date: May 17, 2013

(87) PCT Pub. No.: WO2013/012881
PCT Pub. Date: Jan. 24, 2013

(65) Prior Publication Data
US 2013/0233709 A1    Sep. 12, 2013

Related U.S. Application Data

(60) Provisional application No. 61/572,843, filed on Jul. 20, 2011.

(51) Int. Cl.
*G01N 27/447* (2006.01)
*B82Y 30/00* (2011.01)
*G01N 33/487* (2006.01)

(52) U.S. Cl.
CPC ........ *G01N 27/447* (2013.01); *G01N 33/48721* (2013.01); *B82Y 30/00* (2013.01)
USPC ........... 204/451; 204/401; 204/454; 204/459; 205/778

(58) Field of Classification Search
CPC .................. G01N 33/4871; G01N 33/3278
USPC ................. 204/401, 451, 454, 459, 627
See application file for complete search history.

(56) References Cited

U.S. PATENT DOCUMENTS

| 2002/0056651 | A1 | 5/2002 | Akeson |
| 2004/0144658 | A1* | 7/2004 | Flory ........................ 205/777.5 |
| 2005/0020446 | A1 | 1/2005 | Choudhary et al. |
| 2005/0227239 | A1 | 10/2005 | Joyce |
| 2006/0275911 | A1 | 12/2006 | Wang et al. |
| 2010/0122907 | A1 | 5/2010 | Stanford et al. |
| 2011/0108423 | A1* | 5/2011 | Van Der Zaag et al. ...... 204/547 |

FOREIGN PATENT DOCUMENTS

| EP | 1 646 628 A1 | 4/2006 |
| EP | 1645628 | 4/2006 |
| EP | 2311975 | 10/2009 |
| EP | 2311975 | 4/2011 |
| WO | WO2010007537 | 1/2010 |
| WO | WO 2010/082860 | 7/2010 |
| WO | WO2011097171 | 8/2011 |
| WO | WO2013012881 | 1/2013 |

OTHER PUBLICATIONS

Pedone D et al. "Fabrication and electrical characterization of a porecacitypore device . . . " J. Physics: Condensed Matter. Inst. Physics Pub. Bristol, GB.

* cited by examiner

*Primary Examiner* — Luan Van
*Assistant Examiner* — Steven Rosenwald
(74) *Attorney, Agent, or Firm* — Adam Warwick Bell; Matthew Rupert Kaser

(57) ABSTRACT

Provided is a device comprising an upper chamber, a middle chamber and a lower chamber, wherein the upper chamber is in communication with the middle chamber through a first pore, and the middle chamber is in communication with the lower chamber through a second pore, wherein the first pore and second pore are about 1 nm to about 100 nm in diameter, and are about 10 nm to about 1000 nm apart from each other, and wherein each of the chambers comprises an electrode for connecting to a power supply. Methods of using the device are also provided, in particular for sequencing a polynucleotide.

29 Claims, 3 Drawing Sheets

DUAL-PORE DEVICE

This invention was made with government support under grant number 0845766, awarded by the national Science foundation. The government has certain rights in this invention.

CROSS REFERENCE TO RELATED APPLICATIONS

This application claims the benefit under 35 U.S.C. §119(e) of U.S. Provisional Application Ser. No. 61/572,843 filed Jul. 20, 2011, the content of which is incorporated by reference in its entirety into the present disclosure.

BACKGROUND

A nanopore is a nano-scale opening that forms naturally as a protein channel in a lipid membrane (a biological pore), or is engineered by drilling or etching the opening in a solid-state substrate (a solid-state pore). When such a nanopore is incorporated into a nanodevice comprising two chambers which are separated by the nanopore, a sensitive patch-clamp amplifier can be used to apply a trans-membrane voltage and measure ionic current through the pore.

Nanopores offer great promise for inexpensive whole genome DNA sequencing. In this respect, individual DNA molecules can be captured and driven through the pore by electrophoresis, with each capture event detected as a temporary shift in the ionic current. The sequence of a DNA molecule can then be inferred from patterns within the shifted ionic current record, or from some other auxiliary sensor in or near the nanopore, as DNA passes through the pore channel.

In principle, a nanopore sequencer can eliminate the needs for sample amplification, the use of enzymes and reagents used for catalytic function during the sequencing operation, and optics for detection of sequencing progress, some or all of which are required by the conventional sequencing-by-synthesis methods.

Nanopore sensors are purely electrical, and can detect DNA in concentrations/volumes that are no greater than what is available from a blood or saliva sample. Additionally, nanopores promise to dramatically increase the read-length of sequenced DNA, from 450 bases to greater than 10,000 bases.

There are two principle obstacles to nanopore sequencing: (1) the lack of sensitivity sufficient to accurately determine the identity of each nucleotide in a nucleic acid for de novo sequencing (the lack of single-nucleotide sensitivity), and (2) the ability to regulate the delivery rate of each nucleotide unit through the nanopore during sensing. While many research groups are developing and improving nanopores to address obstacle 1, there is no method for addressing obstacle 2 that does not involve the use of enzymes or optics, both of which work only in specialized nanopore techniques and which incur higher complexity and cost compared to purely electrical methods.

SUMMARY

In one embodiment, provided is a device comprising an upper chamber, a middle chamber and a lower chamber, wherein the upper chamber is in communication with the middle chamber through a first pore, and the middle chamber is in communication with the lower chamber through a second pore, wherein the first pore and second pore are about 1 nm to about 100 nm in diameter, and are about 10 nm to about 1000 nm apart from each other, and wherein each of the chambers comprises an electrode for connecting to a power supply.

In one aspect, the first and second pores are substantially coaxial.

In one aspect, the device comprises a material selected from the group consisting of silicon, silicon nitride, silicon dioxide, graphene, carbon nanotubes, $TiO_2$, $HfO_2$, $Al_2O_3$, metallic layers, glass, biological nanopores, membranes with biological pore insert, and combinations thereof.

In one aspect, the first pore and the second pore are about 0.3 nm to about 100 nm in depth.

In one aspect, the power supply is configured to provide a first voltage between the upper chamber and the middle chamber, and a second voltage between the middle chamber and the lower chamber, and wherein the first voltage and the second voltage are independently adjustable.

In one aspect, the power supply comprises a voltage-clamp system or a patch-clamp system to generate each of the first and second voltages. In one aspect, the middle chamber is adjusted to be ground relative to the two voltages. In one aspect, the middle chamber comprises a medium for providing conductance between each of the pores and the electrode in the middle chamber.

In some aspects, the power supply, such as the voltage-clamp system or the patch-clamp system, is further configured to measure the ionic current through each of the pores.

Another embodiment provides a device comprising an upper chamber, a middle chamber and a lower chamber, wherein the upper chamber is in communication with the middle chamber through a first pore, and the middle chamber is in communication with the lower chamber through a second pore, and wherein the first pore and second pore are about 1 nm to about 100 nm in diameter, and are about 10 nm to about 1000 nm apart from each other; and an electrode in each of the chambers for connecting to a voltage-clamp or patch-clamp system to apply a voltage across and measuring ionic current through each of the pores, wherein the electrode in the middle chamber is connected to a common ground of the two voltage-clamp or patch-clamp systems.

Also provided, in one embodiment, is a method for controlling the movement of a charged polymer through a pore, comprising: (a) loading a sample comprising a charged polymer in one of the upper chamber, middle chamber or lower chamber of the device of any of the above embodiments, wherein the device is connected to a voltage-clamp or patch-clamp system for providing a first voltage between the upper chamber and the middle chamber, and a second voltage between the middle chamber and the lower chamber; (b) setting an initial first voltage and an initial second voltage so that the polymer moves between the chambers, thereby locating the polymer across both the first and second pores; and (c) adjusting the first voltage and the second voltage so that both voltages generate force to pull the charged polymer away from the middle chamber, wherein the two voltages are different in magnitude, under controlled conditions, so that the charged polymer moves across both pores in one direction and in a controlled manner.

In one aspect, the controlled manner of delivery is established by active control or feedback control of the first or second or both voltages, with either or both as a feedback function of the first or second or both ionic current measurements. A non-limiting example includes keeping the second voltage constant, and using the second ionic current as feedback for feedback or active control of the first voltage, to established controlled delivery of a charged polymer in either direction. Accordingly, in one aspect, the first voltage is adjusted based on a measured ionic current across the second pore.

In one aspect, the sample is loaded into the upper chamber and the initial first voltage is set to pull the charged polymer from the upper chamber to the middle chamber and the initial second voltage is set to pull the polymer from the middle chamber to the lower chamber.

In another aspect, the sample is loaded into the middle chamber and the initial first voltage is set to pull the charged polymer from the middle chamber to the upper chamber and the initial second voltage is set to pull the charged polymer from the middle chamber to the lower chamber.

In one aspect, the charged polymer is a polynucleotide or a polypeptide. In one aspect, the charged polymer is a polynucleotide such as, but not limited to, a double-stranded DNA, single-stranded DNA, double-stranded RNA, single-stranded RNA, or DNA-RNA hybrid.

In one aspect, the adjusted first voltage and second voltage at step (c) are about 10 times to about 10,000 times as high, in magnitude, as the difference between the two voltages.

In one aspect, the method further comprises identifying a monomer unit of the polymer by measuring an ionic current across one of the pores when the monomer unit passes that pore. In one aspect, the monomer unit is a nucleotide. In another aspect, the monomer unit is a nucleotide pair. Single nucleotides and nucleotide pairs, in some aspects, can be detected in one molecule. For instance, such a molecule can have a duplex segment in a longer and otherwise single-stranded polynucleotide, with the duplex formed partially or fully by Watson-Crick complementary base pairing.

In one aspect, the monomer is bound to a molecule, such as a DNA-binding protein, or a nano-particle. Non-limiting examples of DNA-binding proteins include RecA and sequence-specific DNA-binding protein such as phage lambda repressor, NF-κB and p53. Non-limiting examples of nano-particles include quantum dots and fluorescent labels.

In one aspect, the polymer is attached to a solid support, such as a bead, at one end of the polymer.

Yet another embodiment provides a method for determining the sequence of a polynucleotide, comprising: (a) loading a sample comprising a polynucleotide in the upper chamber of the device of any of the above embodiments, wherein the device is connected to a voltage-clamp or patch-clamp system for providing a first voltage between the upper chamber and the middle chamber, and a second voltage between the middle chamber and the lower chamber, wherein the polynucleotide is optionally attached to a solid support at one end of the polynucleotide; (b) setting an initial first voltage and an initial second voltage so that the polynucleotide moves from the upper chamber to the middle chamber and from the middle chamber to the lower chamber, thereby locating the polymer across both the first and second pores; (c) adjusting the first voltage and the second voltage so that both voltages generate force to pull the polynucleotide away from the middle chamber, wherein the two voltages are different in magnitude, under controlled conditions, so that the polynucleotide moves across both pores in one direction and in a controlled manner; and (d) identifying each nucleotide of the polynucleotide that passes through one of the pores, by measuring an ionic current across the pore when the nucleotide passes that pore.

BRIEF DESCRIPTION OF THE DRAWINGS

The figures of the accompanying drawings describe provided embodiments by way of illustration only, in which.

Figure 1:
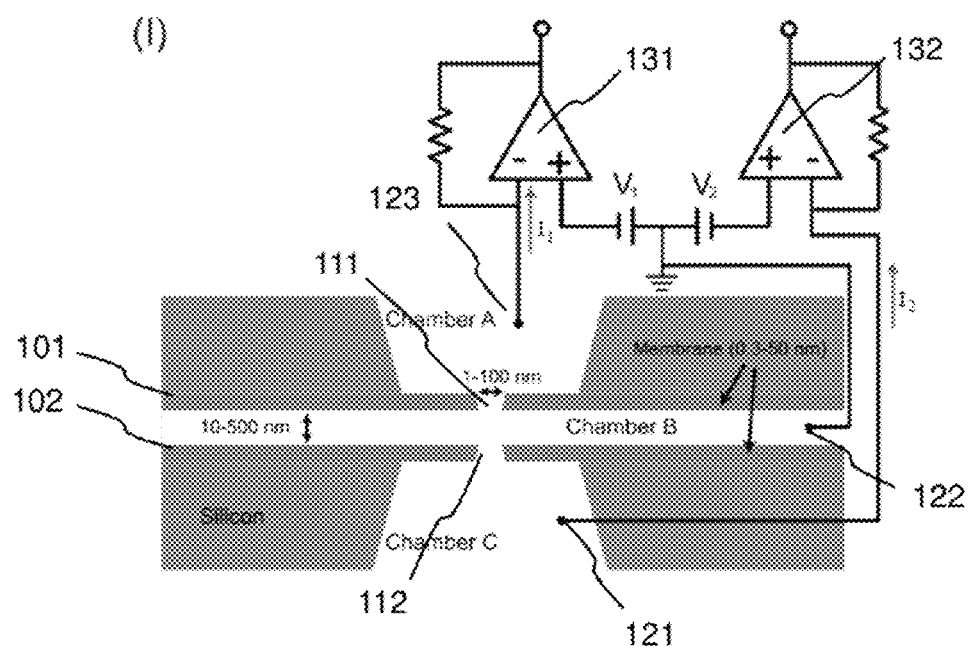
FIG. 1(I)-(III) illustrate a two-pore (dual-pore) device. (I) Schematic of dual-pore chip and dual-amplifier electronics configuration for independent voltage control ($V_1$, $V_2$) and current measurement ($I_1$, $I_2$) of each pore. Chambers (A-C) are volumetrically separated except by common pores. Feasible chip parameters are an inter-pore distance 10-500 nm, membrane thickness 0.3-50 nm, and pore diameters 1-100 nm. (II) Electrically, $V_1$ and $V_2$ are principally across each nanopore resistance, by constructing a device that minimizes all access resistances to effectively decouple $I_1$ and $I_2$. (III) Competing voltages will be used for control, with arrows (200) showing the direction of each voltage force. Each chamber contains an electrode (121, 122 and 123) for connecting to a power supply. Assuming pores with identical voltage-force influence and using $|V_1|=|V_2|+\delta V$, the value $\delta V>0$ ($<0$) is adjusted for tunable motion in the $V_1$ ($V_2$) direction. In practice, although the voltage-induced force at each pore will not be identical with $V_1=V_2$, calibration experiments can identify the required voltage bias that will result in equal pulling forces, for a given two-pore chip, and variations around that bias can then be used for directional control.
Figure 1:
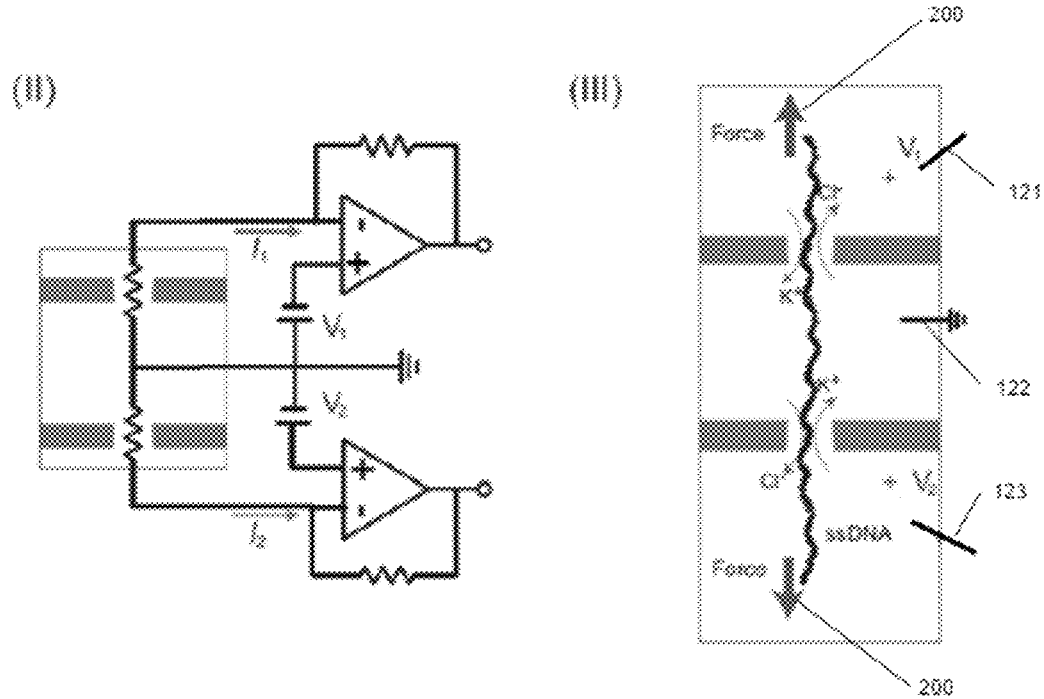

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION

Throughout this application, the text refers to various embodiments of the present nutrients, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

Also throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

As used in the specification and claims, the singular form "a", "an" and "the" include plural references unless the context clearly dictates otherwise. For example, the term "an electrode" includes a plurality of electrodes, including mixtures thereof.

As used herein, the term "comprising" is intended to mean that the devices and methods include the recited components or steps, but not excluding others. "Consisting essentially of" when used to define devices and methods, shall mean excluding other components or steps of any essential significance to the combination. "Consisting of" shall mean excluding other components or steps. Embodiments defined by each of these transition terms are within the scope of this invention.

All numerical designations, e.g., distance, size, temperature, time, voltage and concentration, including ranges, are approximations which are varied (+) or (−) by increments of 0.1. It is to be understood, although not always explicitly stated that all numerical designations are preceded by the term "about". It also is to be understood, although not always explicitly stated, that the components described herein are merely exemplary and that equivalents of such are known in the art.

Two-Pore Device

One embodiment of the present disclosure provides a two-pore device. The device includes three chambers and two pores that enable fluid communication between the chambers. Further, each of the chambers contains an electrode for connecting to a power supply so that a separate voltage can be established across each of the pores between the chambers.

In accordance with one embodiment of the present disclosure, provided is a device comprising an upper chamber, a middle chamber and a lower chamber, wherein the upper chamber is in communication with the middle chamber through a first pore, and the middle chamber is in communication with the lower chamber through a second pore, wherein the first pore and second pore are about 1 nm to about 100 nm in diameter, and are about 10 nm to about 1000 nm apart from each other, and wherein each of the chambers comprises an electrode for connecting to a power supply.

With reference to FIG. 1(I), the device includes an upper chamber (Chamber A), a middle chamber (Chamber B), and a lower chamber (Chamber C). The chambers are separated by two separating layers or membranes (101 and 102) each having a separate pore (111 and 112). Further, each chamber contains an electrode (121, 122 and 123) for connecting to a power supply. It is apparent that the annotation of upper, middle and lower chamber is in relative terms and does not indicate that, for instance, the upper chamber is placed above the middle or lower chamber relative to the ground, or vice versa.

Each of the pores (111 and 112) independently has a size that allows a small or large molecule or microorganism to pass. In one aspect, each pore is at least about 1 nm in diameter. Alternatively, each pore is at least about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm or 100 nm in diameter.

In one aspect, the pore is no more than about 100 nm in diameter.

Alternatively, the pore is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 or 10 nm in diameter.

In one aspect, the pore has a diameter that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In some aspects, the pore has a substantially round shape. "Substantially round", as used here, refers to a shape that is at least about 80 or 90% in the form of a cylinder. In some embodiments, the pore is square, rectangular, triangular, oval, or hexangular in shape.

Each of the pores (111 and 112) independently has a depth. In one aspect, each pore has a depth that is least about 0.3 nm. Alternatively, each pore has a depth that is at least about 0.6 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, or 90 nm.

In one aspect, each pore has a depth that is no more than about 100 nm. Alternatively, the depth is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 or 10 nm.

In one aspect, the pore has a depth that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In one aspect, the pores are spaced apart at a distance that is between about 10 nm and about 1000 nm. In one aspect, the distance is at least about 10 nm, or alternatively at least about 20 nm, 30 nm, 40 nm, 50 nm, 60 nm, 70 nm, 80 nm, 90 nm, 100 nm, 150 nm, 200 nm, 250 nm, or 300 nm. In another aspect, the distance is no more than about 1000 nm, 900 nm, 800 nm, 700 nm, 600 nm, 500 nm, 400 nm, 300 nm, 250 nm, 200 nm, 150 nm, or 100 nm. In yet another aspect, the distance is between about 20 nm and about 800 nm, between about 30 nm and about 700 nm, between about 40 nm and about 500 nm, or between about 50 nm and about 300 nm.

The two pores can be arranged in any position so long as they allow fluid communication between the chambers and have the prescribed size and distance between them. In one aspect, the pores are placed so that there is no blockage directly between them. Still, in one aspect, the pores are substantially coaxial, as illustrated in FIG. 1(I).

In one aspect, the device, through the electrodes in the chambers, is connected to one or more power supply. In some aspects, the power supply is comprised of a voltage-clamp or a patch-clamp for supplying the voltage across each pore, which can also measure the current through each pore independently. In this respect, the power supply can set the middle chamber to a common ground for both voltage sources. In one aspect, the power supply is configured to provide a first voltage between the upper chamber (e.g., Chamber A in FIG. 1(I)) and the middle chamber (e.g., Chamber B in FIG. 1(I)), and a second voltage between the middle chamber and the lower chamber (e.g., Chamber C in FIG. 1(I)).

In some aspects, the first voltage and the second voltage are independently adjustable. In one aspect, the middle chamber is adjusted to be ground relative to the two voltages (illustrated in FIG. 1(I-III)). In one aspect, the middle chamber comprises a medium for providing conductance between each of the pores and the electrode in the middle chamber. In one aspect, the middle chamber comprises a medium for providing a resistance between each of the pores and the electrode in the middle chamber. Keeping such a resistance sufficiently small, relative to the nanopore resistances, is useful for decoupling the two voltages and currents across the pores, which is helpful for the independent adjustment of the voltages.

Adjustment of the voltages can be used to control the movement of charged particles in the chambers. For instance, when both voltages are set in the same direction, a properly charged particle can be moved from the upper chamber to the middle chamber and to the lower chamber, or the other way around, sequentially. Otherwise, a charged particle can be moved from either the upper or the lower chamber to the middle chamber and kept there.

The adjustment of the voltages in the device can be particularly useful for controlling the movement of a large molecule, such as a charged polymer, that is long enough to cross both of the pores at the same time. In such an aspect, the movement and the rate of movement of the molecule can be controlled by the relative magnitude and direction of the voltages, which will be further described below.

The device can contain materials suitable for holding liquid samples, in particular, biological samples, and/or materials suitable for nanofabrication. In one aspect, such materials include dielectric materials such as, but not limited to, silicon, silicon nitride, silicon dioxide, graphene, carbon nanotubes, $TiO_2$, $HfO_2$, $Al_2O_3$, or other metallic layers, or any combination of these materials. A single sheet of graphene forms a membrane ~0.3 nm thick, and can be used as the pore-bearing membrane, for example.

Devices that are microfluidic and that house two-pore microfluidic chip implementations can be made by a variety of means and methods. For a microfluidic chip comprised of two parallel membranes, both membranes can be simultaneously drilled by a single beam to form two concentric pores, though using different beams on each side of the membranes is also possible in concert with any suitable alignment technique. In general terms, the housing ensures sealed separation of Chambers A-C. In one aspect, the housing would provide minimal access resistance between the voltage electrodes (two sources and one ground) and the nanopores, to ensure that each voltage is applied principally across each pore.

Figure 2:
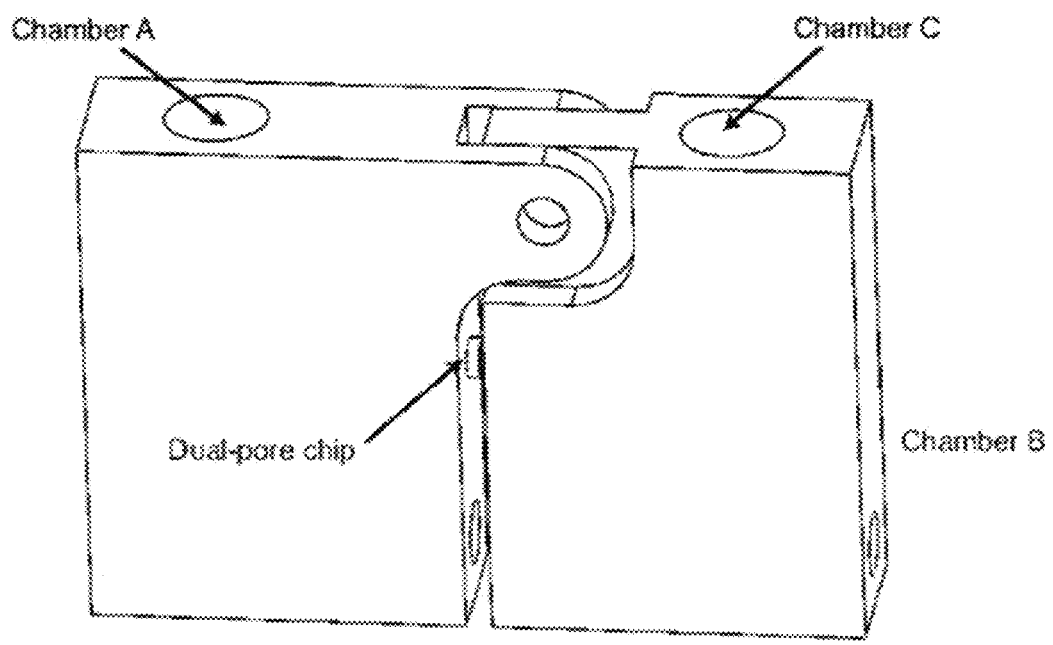
FIG. 2 shows an external view of a two-pore housing device having a Chamber A, Chamber B and Chamber C, each having an opening for fluidic access and sample loading. A dual-pore chip is placed between two gaskets, with each gasket part of each portion of the housing device, and the two portions rotate around a hinge (middle top) to open and close the housing around the chip.

In one aspect, FIG. 2 shows an external view of another embodiment of the device. In FIG. 2, the device contains a microfluidic chip (labeled as "Dual-core chip") comprised of two parallel membranes connect by spacers. Each membrane contains a pore (not shown) drilled by a single beam through the center of the membrane. Further, the device preferably has a Teflon® housing for the chip. The housing ensures sealed separation of Chambers A-C and provides minimal access resistance for the electrolyte to ensure that each voltage is applied principally across each pore.

More specifically, the pore-bearing membranes can be made with TEM (transmission electron microscopy) grids with 5-100 nm thick silicon, silicon nitride, or silicon dioxide windows. Spacers can be used to separate the membrane, using an insulator (SU-8, photoresist, PECVD oxide, ALD oxide, ALD alumina) or an evaporated metal (Ag, Au, Pt) material, and occupying a small volume within the otherwise aqueous portion of Chamber B between the membranes. The holder is seated in an aqueous bath that comprises the largest volumetric fraction of Chamber B. Chambers A and C are accessible by larger diameter channels (for low access resistance) that lead to the membrane seals.

A focused electron or ion beam can be used to drill pores through the membranes, naturally aligning them. The pores can also be sculpted (shrunk) to smaller sizes by applying the correct beam focus to each layer. Any single nanopore drilling method can also be used to drill the pair of pores in the two membranes, with consideration to the drill depth possible for a given method and the thickness of the membranes. Predrilling a micro-pore to a prescribed depth and then a nanopore through the remainder of the membranes is also possible, to further refine membrane thicknesses.

In another aspect, insertion of biological nanopores into solid-state nanopores to form a hybrid pore can be used in either or both nanopores in the two-pore method (Hall et al., *Nat. Nanotech.*, 5(12):874-7, 2010). The biological pore can increase the sensitivity of the ionic current measurements, and are useful when only single-stranded polynucleotides are to be captured and controlled in the two-pore device, e.g., for sequencing.

Controlling Movement of Molecules with a Two-Pore Device

By virtue of the voltages present at the pores of the device, charged molecules can be moved through the pores between chambers. Speed and direction of the movement can be controlled by the magnitude and direction of the voltages. Further, because each of the two voltages can be independently adjusted, the movement and speed of a charged molecule can be finely controlled in each chamber.

For instance, the device can be used to admix two positively charged molecules in a controlled manner. To this end, the first molecule is initially loaded in the upper chamber and the second in the lower chamber. A first voltage across the first port can induce movement of the first molecule into the middle chamber from the upper chamber. Likewise, a second voltage, in the opposite direction to the first voltage, can induce movement of the second molecule into the middle chamber from the lower chamber. Due to the opposite directions of the voltages, both molecules will be kept in the middle chamber so as to react with each other. Further, by adjusting the relative magnitudes of the voltages, the inflow speeds of each molecules can be fine tuned, leading to controlled reaction.

Another example concerns a charged polymer, such as a polynucleotide, having a length that is longer than the combined distance that includes the depth of both pores plus the distance between the two pores. For example, a 1000 bp dsDNA is ~340 nm in length, and would be substantially longer than the 40 nm spanned by two 10 nm-length pores separated by 20 nm. In a first step, the polynucleotide is loaded into either the upper or the lower chamber. By virtue of its negative charge under a physiological condition (~pH 7.4), the polynucleotide can be moved across a pore on which a voltage is applied. Therefore, in a second step, two voltages, in the same direction and at the same or similar magnitudes, are applied to the pores to induce movement of the polynucleotide across both pores sequentially.

At about time when the polynucleotide reaches the second pore, one or both of the voltages can be changed. Since the polynucleotide is longer than the distance covering both pores, when the polynucleotide reaches the second pore, it is also in the first pore. A prompt change of direction of the voltage at the first pore, therefore, will generate a force that pulls the polynucleotide away from the second pore (illustration in FIG. 1(III)).

If, at this point, the magnitude of the voltage-induced force at the first pore is less than that of the voltage-induced force at the second pore, then the polynucleotide will continue crossing both pores towards the second pore, but at a lower speed. In this respect, it is readily appreciated that the speed and direction of the movement of the polynucleotide can be controlled by the directions and magnitudes of both voltages. As will be further described below, such a fine control of movement has broad applications.

Accordingly, in one aspect, provided is a method for controlling the movement of a charged polymer through a pore. The method entails (a) loading a sample comprising a charged polymer in one of the upper chamber, middle chamber or lower chamber of the device of any of the above embodiments, wherein the device is connected to a power supply for providing a first voltage between the upper chamber and the middle chamber, and a second voltage between the middle chamber and the lower chamber; (b) setting an initial first voltage and an initial second voltage so that the polymer moves between the chambers, thereby locating the polymer across both the first and second pores; and (c) adjusting the first voltage and the second voltage so that both voltages generate force to pull the charged polymer away from the middle chamber (voltage-competition mode), wherein the two voltages are different in magnitude, under controlled conditions, so that the charged polymer moves across both pores in either direction and in a controlled manner.

For the purpose of establishing the voltage-competition mode in step (c), the relative force exerted by each voltage at each pore is to be determined for each two-pore device used, and this can be done with calibration experiments by observing the influence of different voltage values on the motion of the polynucleotide (motion can be measured by sensing location-known and detectable features in the polynucleotide, with examples of such features detailed later in this provisional document). If the forces are equivalent at each common voltage, for example, then using the same voltage value at each pore (with common polarity in upper and lower chambers relative to grounded middle chamber) creates a zero net motion in the absence of thermal agitation (the presence and influence of Brownian motion is discussed below). If the forces are not equivalent at each common voltage, then achieving equal forcing requires identification and use of a larger voltage at the pore that experiences a weaker force at the common voltage. Calibration for voltage-competition mode is required for each two-pore device, and would be required for specific charged polymers or molecules for which features that pass through each pore influence the force.

In one aspect, the sample is loaded into the upper chamber and the initial first voltage is set to pull the charged polymer from the upper chamber to the middle chamber and the initial second voltage is set to pull the polymer from the middle chamber to the lower chamber. Likewise, the sample can be initially loaded into the lower chamber.

In another aspect, the sample is loaded into the middle chamber and the initial first voltage is set to pull the charged polymer from the middle chamber to the upper chamber and the initial second voltage is set to pull the charged polymer from the middle chamber to the lower chamber.

In some aspects, the charged polymer is a polynucleotide or a polypeptide. In a particular aspect, the charged polymer is a polynucleotide. Non-limiting examples of polynucleotides include double-stranded DNA, single-stranded DNA, double-stranded RNA, single-stranded RNA, and DNA-RNA hybrids.

In one aspect, the adjusted first voltage and second voltage at step (c) are about 10 times to about 10,000 times as high, in magnitude, as the difference between the two voltages. For instance, the two voltages are 90 mV and 100 mV, respectively. The magnitude of the voltages (~100 mV) is about 10 times of the difference between them, 10 mV. In some aspects, the magnitude of the voltages is at least about 15 times, 20 times, 25 times, 30 times, 35 times, 40 times, 50 times, 100 times, 150 times, 200 times, 250 times, 300 times, 400 times, 500 times, 1000 times, 2000 times, 3000 times, 4000 times, 5000 times, 6000 times, 7000 times, 8000 times or 9000 times as high as the difference between them. In some aspects, the magnitude of the voltages is no more than about 10000 times, 9000 times, 8000 times, 7000 times, 6000 times, 5000 times, 4000 times, 3000 times, 2000 times, 1000 times, 500 times, 400 times, 300 times, 200 times, or 100 times as high as the difference between them.

In one aspect, real-time or on-line adjustments to first voltage and second voltage at step (c) are performed by active control or feedback control using dedicated hardware and software, at clock rates up to hundreds of megahertz. Automated control of the first or second or both voltages is based on feedback of the first or second or both ionic current measurements.

Analysis of Molecules with a Two-Pore Device

The two-pore device of the present disclosure can be used to carry our analysis of molecules or particles that move or are kept within the device by virtue of the controlled voltages applied over the pores. In one aspect, the analysis is carried out at either or both of the pores. Each voltage-clamp or patch-clamp system measures the ionic current through each pore, and this measured current is used to detect the presence of passing charged particle or molecules, or any features associated with a passing charged particle or molecule.

As provided above, a polynucleotide can be loaded into both pores by two voltages having the same direction. In this example, once the direction of the voltage applied at the first pore is inversed and the new voltage-induced force is slightly less, in magnitude, than the voltage-induced force applied at the second pore, the polynucleotide will continue moving in the same direction, but at a markedly lower speed. In this respect, the amplifier supplying voltage across the second pore also measures current passing through the second pore, and the ionic current then determines the identification of a nucleotide that is passing through the pore, as the passing of each different nucleotide would give rise to a different current signature (e.g., based on shifts in the ionic current amplitude). Identification of each nucleotide in the polynucleotide, accordingly, reveals the sequence of the polynucleotide.

In some aspects, repeated controlled delivery for re-sequencing a polynucleotide further improves the quality of sequencing. Each voltage is alternated as being larger, for controlled delivery in each direction. Also contemplated is that the two currents through the two pores can be correlated to improved accuracy. It is contemplated that Brownian motion may cause fluctuations in the motion of a molecule, affecting controlled delivery of the molecule. Such an effect, however, can be minimized or avoided by, e.g., during DNA sequencing, repeated controlled delivery of the DNA and averaging the sequencing measurements. Still further, it is contemplated that the impact of Brownian motion on the controlled motion of large molecules, such as polynucleotides and polypeptides, would be insignificant in particular when competing forces are pulling the larges molecules apart, generating tension within the molecule.

Such a method provides a ready solution to problems that have not been solved in the prior art.

For instance, it is known that there are two competing obstacles to achieve the controlled delivery and accurate sensing required for nanopore sequencing. One is that a relatively high voltage is required, at the pore, to provide enough sequencing sensitivity. On the other hand, high voltages lead to fast passing of a polynucleotide through the pore, not allowing sufficient time for identification of each nucleotide.

More specifically, the nanopore sequencing platform requires that the rate of polynucleotide passage through the pore be controlled to 1 ms/nucleotide (nt) or slower, while still generating a sequence-sensitive current. This requires sufficiently high signal-to-noise for detecting current signatures (high voltage is better), but sufficiently slow motion of the molecule through the pore to ensure measurements are within the recording bandwidth (low voltage is better). In single pore implementations, polynucleotide speed is proportional to voltage, so higher voltage is better for sensing but worse for reducing polynucleotide speed: rates are 1 μs/nt and faster (>1000 times too fast) at voltages that promote polynucleotide capture. On the other hand, lower voltages reduce sensing performance, and also increase the relative contribution of rate fluctuations caused by Brownian motion that will undermine read accuracy.

Other than what is described herein, there are currently no methods for addressing these obstacles that do not involve the use of enzymes or optics, both of which work only in specialized nanopore techniques.

Several approaches have been proposed to address the problem associated with the lack of sensing capability, and under low voltages. One is to engineer biological nanopores to improve their sensitivity. Another is to use graphene membranes, which as a single sheet are thinner than the distance between nucleotides in ssDNA. Still another is the use of an auxiliary current measured in close proximity to the nanopore (e.g., tunneling currents).

Biological nanopores have been tested in the first approach. The α-hemolysin nanopore is the most commonly used biological pore in research. Studies have shown that α-hemolysin can resolve single nucleotide substitutions in homopolymers and abasic (1',2'-dideoxy) residues within otherwise all-nucleobase DNA. However, single nucleotide sensitivity is not possible in heteromeric DNA with wild-type (WT) α-hemolysin, for which the ionic current is influenced by ~10 nucleotides in the channel. Protein engineering of α-hemolysin has been used to improve its sensitivity for DNA analysis and sequencing. One such mutant pore uses α-hemolysin with a covalently attached molecular adapter (Clarke et al., *Nat. Nanotech,* 4(4):265-70, 2009) that is capable of discriminating the four nucleoside 5'-monophosphate molecules with high accuracy. However, this mutant pore does not appear to have sensitivity for sequencing intact heteromeric ssDNA that passes through the pore.

Another exemplary biological pore is MspA, which has a funnel-like shape that focuses the sensitivity of the ionic current to the bottom of the channel. Moreover, achieving rate reduction of DNA through MspA and α-hemolysin can be achieved by using enzymes. As shown in FIG. 1 of (Manrao et al., *Nature Biotechnology,* 30:349-53, 2012), rate reduction of DNA through is achieved with the enzyme perched on the MspA nanopore. However, this results in non-deterministic sensing durations, repeated reads induced by backtracking, and an inability to sense homopolymeric regions. The mechanism of phi29 polymerase mediated DNA translocation was developed in (Cherf et al., *Nat. Biotech.,* 30(4):344-8, 2012) on α-hemolysin and implemented on the more sensitive MspA nanopore (Manrao et al., *Nature Biotechnology,* 30:349-53, 2012). Step-wise rates of polymerization-catalyzed translocation are 2.5-40 nt/s, meeting the requirements for DNA rate reduction. However, while enzymes on biopores can reduce the rate of translocation, there is lack of control over the dwell time of each nucleotide, which will make blind tracking of repeats very difficult, and challenging to differentiate from long pauses on a single nucleotide read. In terms of sensitivity, as shown in FIG. 3 of (Manrao et al., *Nature Biotechnology,* 30:349-53, 2012), reading a repetitive DNA template can be achieved with phi29 on MspA. The FIG. 3*a*) shows an example trace for a DNA template composed of repeated CAT trinucleotides, with the exception of one CAG triplet in the middle of the sequence. The * represent "toggles" detected (by human analysis) as repeated transitions between two levels, which are intrinsic to the enzyme-based control method and incur read errors. The Figures (3*b*) also shows Idealization of (3*a*), with mean currents of levels aligned with the known DNA sequence, and removing disparity of measured durations shown in (3*a*). Idealization shows a repeating pattern of three levels interrupted by the single dG substitution. Four levels are affected by the single dG with the largest deviations closest to the substitution, suggesting residual current is principally influenced by ~4 nucleotides. That the ionic current through MspA is influenced by ~4 nucleotides most proximal to the limiting aperture adds considerable complexity to identifying the sequence. While one would ideally build a library of distinct current amplitudes that map to each of the $4^4=256$ combinations, as suggested in the art, such a library will be difficult to achieve. The reason is that identifying step transitions in channel current recordings requires a signal-to-noise ratio (SNR) of at least 2 with half-amplitude methods (SNR≥1.5 for Markov-based methods). With RMS noise of 0.5 pA at recording bandwidths, amplitudes shifts must be at least 1 pA to have the required SNR, resulting in only ~40 detectable levels within the amplitude range of 40 pA with MspA (or, at most 53 levels at SNR 1.5). Moreover, fewer than 40 levels will be observed since the range will not be uniformly utilized, and while further filtering could reduce noise to add amplitude discrimination it also results in missing more of the faster ssDNA motion transitions that are already present.

Presently, there is no nanopore for which ionic current sensing can provide single-nucleotide sensitivity for nucleic acid sequencing. Still, improvements to the sensitivity of biological pores and solid-state pores (graphene) are active and ongoing research fields. One issue is that ionic current sensing does not permit direct tracking of progress through homolymeric regions (base repeats), since there is no distinct signal-per-nucleotide of motion of homopolymeric ssDNA through the pore. Tracking repeats is essential, for example, since deletions and insertions of specific mononucleotide repeats (7, 9 nt) within human mitochondrial DNA have been implicated in several types of cancer (Sanchez-Cespedes, et al., *Cancer Research,* 61(19):7015-7019, 2001). While enzymes on biopores can reduce the rate of translocation, there is lack of control over the dwell time of each nucleotide. On the other hand, using a constant delivery rate with two-pore control, non-deterministic pauses are eliminated, and accurate estimation of repeat lengths can be made. Re-reading the repeat section many times can also improve the estimation errors and identify error bounds, and this can be done without having to reverse the polymerization chemistry caused by enzymes.

A recent study showed that, with a single nanopore, reduced rates cannot be achieved by merely reducing the voltage (Lu et al., *Biophysical Journal,* 101(1):70-9, 2011). Instead, as voltage is reduced, the rates of a single-stranded DNA (ssDNA) become more random (including backtracking), since Brownian motion becomes an increasing contributor to velocity fluctuations. The study also shows that high voltage force is required to suppress Brownian-motion induced velocity fluctuations that will otherwise confound sequencing measurements, even when using an idealized single-nucleotide-sensitive nanopore sensor.

The sequencing method provided in the present disclosure, based on a two-pore device, provides a ready solution to these problems and additional advantages over the existing methods. In concert with one or two pores that have sufficient sensitivity for sequencing, at high or low voltage, the two pore control solves the sequencing rate control problem of single nanopore implementations. Such pores can include biological pores housed in solid-state substrates, biological pores in membranes formed across solid-state substrates, or solid-state pores (e.g., in graphene, silicon, or other substrates). In one aspect, an enzyme such as phi29 on a biological pore such as MspA can be used at one or both pores, with high voltages used to generate large signals for sequencing and a low differential voltage that generates a force on each enzyme that is sufficient to hold the enzymes in position atop each pore and permit polymerization-catalyzed DNA motion, but not large enough to stall or dissociate the enzymes. Such a configuration can improve the methods in Cherf et al., *Nat. Biotech.*, 30(4):344-8, 2012 and Manrao et al., *Nature Biotechnology*, 30:349-53, 2012, by significantly boosting the measurement signal, and permitting two pores to read one stand of DNA at the same time.

In addition, the method of the present disclosure can generate sufficiently high voltage at the pore to ensure detection sensitivity at the pore using ionic current sensing. It is plausible that high voltage would suppress Brownian motion enough to ensure constant rates through each pore, and configuration of the DNA outside each pore will affect the energetics of motion of DNA in either direction. Additionally, the voltage competition used in the method (FIG. 1(III)) can be tuned so that the molecule spends sufficient time in the pore to allow analysis of the molecule. Still further, the present method is free of the need for enzymes, optics, or attachments to the DNA. Therefore, the method provides high signal-to-noise detection currents through the nanopore while regulating the molecule delivery rate, a capability that is not possible with single nanopore implementations.

The method can be used to identify the composition of monomers in a charged polymer. In one aspect, the monomer unit is a nucleotide when the polymer is a single stranded DNA or RNA. In another aspect, the monomer unit can be a nucleotide pair, when the polymer is double stranded.

In one aspect, the method can be used to identify a modification to the polymer, such as a molecule bound to a monomer, in particular when the bound molecule is charged. The bound molecule does not have to be charged, however, as even a neutral molecule can change the ionic current by virtue of its size.

In another aspect, the modification comprises the binding of a molecule to the polymer. For instance, for a DNA molecule, the bound molecule can be a DNA-binding protein, such as RecA, NF-κB and p53. In yet another aspect, the modification is a particle that binds to a particular monomer or fragment. For instance, quantum dots or fluorescent labels bound to a particular DNA site for the purpose of genotyping or DNA mapping can be detected by the device. Accordingly, the device of the present disclosure provides an inexpensive way for genotyping and DNA mapping as well, without limitation.

In one aspect, the polymer is attached to a solid support, such as a bead, at one end of the polymer.

Also provided, in one embodiment, is a method for determining the sequence of a polynucleotide, comprising: (a) loading a sample comprising a polynucleotide in the upper chamber of the device of any of the above embodiments, wherein the device is connected to a power supply for providing a first voltage between the upper chamber and the middle chamber, and a second voltage between the middle chamber and the lower chamber, wherein the polynucleotide is optionally attached to a solid support at one end of the polynucleotide; (b) setting an initial first voltage and an initial second voltage so that the polynucleotide moves from the upper chamber to the middle chamber and from the middle chamber to the lower chamber, thereby locating the polymer across both the first and second pores; (c) adjusting the first voltage and the second voltage so that both voltages generate force to pull the polynucleotide away from the middle chamber, wherein the two voltages are different in magnitude, under controlled conditions, so that the polynucleotide moves across both pores in one direction and in a controlled manner; and (d) identifying each nucleotide of the polynucleotide that passes through one of the pores, by measuring an ionic current across the pore when the nucleotide passes that pore.

EXAMPLES

The present technology is further defined by reference to the following examples. It will be apparent to those skilled in the art that many modifications, both to threads and methods, may be practiced without departing from the scope of the current invention.

Example 1

Capture and Control of Individual dsDNA Molecules in Pores

This example shows that capture of DNA into each pore in a two-pore device is readily detected as shift in each independent ionic pore current measured.

This example demonstrates dual-pore capture using dsDNA with and without a bead attached to one end. Experiments with bead-tethered ssDNA can also be explored.

Upon capture and stalling of the DNA, the pore voltage nearest the bead (V1, FIG. 1(I) in the case of capture from chamber A) can be reversed and increased until the competing force on the DNA draws it back toward chamber A. The ionic current in either pore can readily detect capture and exit of the DNA during the experiment.

When a bead is used, the bead has a proper size that prevents the bead from passing either or both of the pores. Methods that ensure a 1 to 1 bead-DNA ratio have been developed in the art. For example, monovalent streptavidin-coated Quantum dots (QDs; QD655, Invitrogen) conjugated to biotinylated DNA duplexes (or ssDNA) can provide beads in the 20-30 nm diameter range, with larger beads (30-100 nm) possible by using gold particles or latex. The influence of bead on hydrodynamics and charge, as it relates to capture rate, can be considered in designing the experiments.

Without beads, dsDNA passes through a pore at ~0.1 ms/kbp. DNA of lengths 500 bp and 4 kbp, and λ-phage dsDNA molecules (~48 kbp) can be used. DNA samples can be delivered from chamber A into both pores, using a common voltage polarity for each pore to promote capture from chamber A and passage through chamber B into chamber C (FIG. 1(I)). The large persistence length of dsDNA (one Kuhn length is 100 nm) ensures that the DNA segment inside each pore is likely fully extended and rod-like. Voltage and ionic concentration can be varied to identify adequate capture rates. Different buffered ionic concentrations can also be used in each chamber to enhance or alter capture rates, and conductance shift values that register the presence of DNA in each pore.

Using nanopore diameters 10 nm and larger minimizes the interaction (e.g., friction and sticking) between dsDNA and the nanopore walls. For larger pores, although dsDNA can be captured in an unfolded and folded configurations, the single-file (unfolded) configuration is more likely at higher voltages, and with shorter (53 kbp) dsDNA. For an inter-pore distance of 500 nm or less, it is contemplated that the probability of dual-pore capture, following capture at the first pore (between chambers A and B) is very high, for voltages of at least 200 mV in 1 M KCl.

The radial distance within which voltage influence dominates thermal diffusion, and leads to capture with high likelihood, has been estimated to be at least 900 nm (larger than the inter-pore distance) for a range of pore sizes (6-15 nm diameter), voltages (120-500 mV), and with dsDNA at least 4 kbp in length (Gershow and Golovchenko, *Nature Nanotechnology*, 2:775-779, 2007). These findings support a high likelihood of prompt dual-pore capture of dsDNA, following single (first) pore capture of the dsDNA.

The capture and control of DNA through the two pores can benefit from active control hardware and real-time algorithms. The inventors have developed active control hardware/software for DNA control. See, for example, Gyarfas et al, *Biophys. J.*, 100:1509-16, 2011); Wilson et al., *ACS Nano.*, 3(4):995-1003, 2009; and Benner et al., *Nat. Nanotech.*, 2(11):718-24, 2007. A useful software is the LabVIEW software (Version 8, National Instruments, Austin, Tex.), implemented on an FPGA (field-programmable gate array) system (PCI-7831 R, National Instruments)). The referenced FPGA can control up to 4 amplifiers simultaneously. Further, the Axon Digidata 1440A Data Acquisition System used to digitize and log data onto a PC has 16 input channels, enough to record voltage and current for up to 8 amplifiers in parallel. Other real-time operating system in concert with hardware/software for real-time control and measurement could also be used for controlling the amplifiers, and digitizing and logging the data.

The inventors have also developed a low-noise voltage-clamp amplifier termed the "Nanoclamp," (Kim et al., *IEEE Trans. On Biom. Circ. And Syst*. In press, May 2012; Kim et al., *Elec. Lette.*, 47(15):844-6, July, 2011; and Kim et al., *Proceedings of the IEEE International SoC Design Conference (ISOCC)*, November 2010) to functionalize and optimize the use of one or more nanopores in small-footprint and multi-channel devices. Any other commercial bench-top voltage-clamp or patch-clamp amplifier, or integrated voltage-clamp or patch-clamp amplifier could be used for two pore control and measurement.

For a variety of solid-state pore materials and diameters, 0.1-10 kbp takes ~1 ms to translocate. With a FPGA-controlled amplifier, one can detect capture and initiate competing voltage control within 0.020 ms, much faster than the 1 ms total passage time of 1 kbp DNA; thus, triggering the control method before DNA escapes (with no bead attachment) also has high likelihood. As demonstration of control, the time to, and direction of, exit of the molecule from the pores can be demonstrated as a function of the magnitude of and difference between the competing voltages (FIG. 1(III)). In single pore experiments, large fluctuations in the velocity of long (1 kbp) dsDNA through the pore are experimentally observed, and these fluctuations are too large to be attributed to diffusional Brownian motion. In (Lu, et al., *Biophysical Journal*, 101(1): 70-79, 2011), the dominant source of the net velocity fluctuations (i.e., DNA length divided by total passage time) was modeled as being due to viscous drag induced by the voltage affecting portions of the DNA not yet in the pore, in addition to portion in the pore, where the voltage region of attraction extends. The model matched experimental data reasonably well. Notably, if the center of mass of the dsDNA is colinear with the pore upon capture, net velocity is faster, but if it is offset from the pore, net velocity is slower. When competing voltages are engaged in the two-pore device, dsDNA velocities will not be affected by this viscous-drag-induced perturbation, unless the voltage difference is sufficiently high. The reason is that, after dsDNA capture through both pores and competing voltage is engaged, the dsDNA between the pores will be fully extended and rod-like, and therefore cannot engage in creating structures near either interior pore entry.

On the other hand, dsDNA structures on the exterior sides of the pores are constantly forced by each local pore voltage away from the middle channel, and are thus less likely to confound the pore entry kinetics. Such structure may affect the controlled delivery kinetics, and calibration experiments can be used to quantify this.

Force uncertainty induced by random transverse DNA motion is likely minimal. Additionally, the voltage force causes an electroosmotic flow (EOF) in the opposite direction of DNA motion, causing the DNA to move slower than it would in the absence of the induced counterion flow. Since different radial positions of the molecule can give rise to different EOF fields in the nanopore, one issue is whether the effective charge density and therefore the net driving force vary enough during fluctuations in DNA radial position to induce speed fluctuations. It is believed that the effective charge density of DNA in 1M KCl is stable for a distance of 1 nm or more between the pore wall and the DNA.

Additionally, SiN nanopores have a negative surface charge that intrinsically repels DNA. Thus, although the molecule will undergo radial position fluctuations, by using SiN pores with diameter greater than a few nanometers, it is likely that each constant voltage value will result in a constant effective force at each of the two pores, and thus a constant velocity in the direction of larger force when using two competing voltages in the two-pore setup. Treatment of other pore material surfaces can produce comparable effects to that of SiN.

Velocity uncertainty induced by random translational DNA motion that is caused by Brownian motion may be reduced by increasing the competing voltages. Experiments can be carried out to determine whether such reduction will occur. A single-nanopore study (Lu, et al., *Biophysical Journal*, 101(1):70-79, 2011) supports that increasing the competing forces can reduce uncertainty caused by Brownian motion. The study analyzed the velocity fluctuations caused by Brownian motion, which occur on fast (nanosecond) time scales, and the sequencing errors that result from such fluctuations. Assuming a hypothetical and idealized single-nucleotide sensor (noise-free detection at >22 MHz bandwidth), Brownian motion alone results in 75% read error. The relevant parameter for predicting the error is $k_B T/F^*(0.34 \text{ nm})$, which is the ratio of thermal energy to the work done to translocate the DNA the distance a between nucleotides (0.34 nm). In the ratio, force $F=V\lambda$ is the voltage V driving DNA with charge density $\lambda$ (0.2 e$^-$/bp for dsDNA). For the present control method, increasing the voltage 50× results in 5% read error, with higher voltage further improving errors. With a single pore, however, since mean velocity $\bar{v}$ is $F^*d/(k_B T)$ with diffusion constant d, DNA speed also increases with F, placing even more unrealistic demands on the sequencing bandwidth.

To maintain the 22 MHz bandwidth, a 50× increase in force with a single nanopore would have to be paired with a 50× increase in solution viscosity to maintain the same $\bar{v}$. Practically, however, 22 MHz bandwidth is already much higher than any experimental nanopore platform has demonstrated, or promises to demonstrate, for single-nucleotide sequencing. Moreover, increasing viscosity can slow DNA only up to 10× (Fologea, et al., *Nano Lett.*, 5(9):1734-7, 2005) with single nanopores. Using the two-pore platform, each voltage can be kept sufficiently high, and this may suppress fluctuations caused by Brownian motion, while the differential voltage that determines the net DNA speed can be adjusted to ensure control rates are within actual sequencing bandwidths (nominally 1 kHz). An alternative method of suppressing Brownian motion induced velocity fluctuations is to use feedback control. In one aspect, with 10 kHz bandwidth of the second pore current feedback to actuation of the first pore voltage at 10 kHz bandwidth, Brownian motion can be compensated to control detectable features on the DNA to remain in and near the second pore at these kHz closed-loop bandwidths. This capability is a one-dimensional analogue to the anti-Brownian electrokinetic (ABEL) trap that suppressed Brownian motion in two spatial dimensions and works by optical forcing of beads attached to molecules at Hz closed-loop bandwidths (Wang and Moerner, *ACS Nano*, 5:5792-9, 2011).

Example 2

Detection and Localization of RecA Filaments Bound to DNA

This example shows that the two-pore device can be used to map the binding of a DNA-binding protein to dsDNA, and for proteins that have or do not bind to specific sequences.

As demonstrated in Example 1, DNA samples can be captured from Chamber A. RecA protein catalyses an ATP-dependent DNA strand-exchange reaction that pairs broken DNA with complementary regions of undamaged DNA. Using a poorly hydrolyzable ATP analogue ATP γS, RecA filaments bound to dsDNA are very stable in high salt (e.g., 1M KCl) when first assembled in physiological salt. As an alternative to ATPγS, which is slowly hydrolyzed, this example can also use ADP-AlF4 (aluminum tetrafluoride), which does not turnover at all, and causes RecA to bind more tightly to the DNA.

Detection of RecA filaments bound to λ-DNA through 20-30 nm nanopores has been demonstrated (Kowalczyk et al., *Nano Lett.*, 10(1):324-8, 2010; Smeets et al., *Nano Lett.*, 9(9):3089-95, 2009; and Hall et al. *Nano Lett.*, 9(12):4441-5, 2009], but filaments <20 bp (6 or fewer RecA proteins) in length cannot be resolved using a single nanopore, due to the coupling between translocation rate and measurement SNR.

Initial experiments of this example use bead-bound and unbound λ-DNA that has been exposed to varying concentrations of RecA, to generate DNA that is nearly uncoated, partially coated, and fully coated. Real-time monitoring of each pore current can be used to gauge progress of the controlled delivery, and will be correlated for location mapping of the filaments. Repeated measurements of each DNA will improve accuracy of RecA mapping.

The added charge and bulk, and stability in high salt, when RecA is bound to DNA make it an ideal candidate to attempt detection and location mapping during controlled delivery with the proposed instrument.

Control of RecA-bound DNA can also be attempted without a bead attached to arrest translocation. As with dsDNA experiments in Example 1, active voltage control can be used to promptly initiate competing voltage control before the DNA exits the nanopores. As charged species that bind to DNA affect the mobility of DNA in an electric field, by altering the net charge and stiffness of the DNA, motion control tuning experiments can examine the influence of RecA binding to dsDNA on the force balance used to control the motion of the dsDNA.

This example can demonstrate that the shortest observed filament lengths, at low RecA concentrations, can be measured at high SNR and at sufficiently slow and controlled rates, so that any RecA protein bound in isolation can be detected if present.

The two-pore device therefore provides a completely new single-molecule instrument for basic research, as one could examine the capability to detect binding of additional proteins to the RecA-DNA filament, which would increase the filament width and thus be detected by a decrease in observed current. For example, proteins that bind to the RecA-DNA filament include LexA and bacteriophage lambda repressors, which use RecA to sense the status of the cell and switch on or off downstream regulatory events.

Calibration experiments would involve detecting proteins that bind to specific sequences (locations) on the DNA, so that protein-induced shifts in the current would then permit estimation of the speed and rate control performance of the DNA through the pores. Example proteins that bind to specific sites on dsDNA include Lac repressor (binds to a 21 bp segment), phage lambda repressor (which has multiple operator sites on λ-DNA), and other proteins.

Example 3

Detection and Localization of a Double-Stranded Segment within a Singled-Stranded DNA This example demonstrates the production of up to 10 kb ssDNA with doubled-stranded segments of varying lengths.

In a first step, 10 kbp dsDNA can be created by long range PCR. One end of the strand is biotinylated for bead attachment, and the strands are separated by chemical denaturing. The unbeaded 10 kb ssDNA then serves as the measured strand in two-pore experiments. Complementary single-stranded segments with desired sizes can be created by PCR followed by bead capturing and strand separation.

ssDNA segments of varying lengths and at multiple sites within the measured 10 kb ssDNA can be used, starting with a set of 100 nt segments. Ionic current through a single solid-state pore was used to differentiate dsDNA from ssDNA homopolymers, and purine and pyrimidine homopolymers in (Skinner et al., *Nano Lett.*, 9(8):2953-60, January 2009). Thus, likelihood of differentiating single from double stranded segments in DNA is high at sufficiently high voltage using the two-pore device. Mapping ssDNA vs. dsDNA segments enables nanopore sequencing using the hybridization-assisted method (though this method as proposed relies on a costly hybridization-assisted process), and can be used reveal both location and identity of target DNA sequences over long distances (targeted sequencing). One can also explore the use of Single Strand DNA Binding (SSB) proteins, as beads that will further amplify the ssDNA vs. dsDNA differences in ionic current by binding to the ssDNA and creating a larger impedance than dsDNA.

Example 4

Capture and Control of Long ssDNA and Localization of RecA

This example demonstrates the capture and control of a long ssDNA and the detection and localization of a RecA filament bound to the ssDNA. Additionally, it shows that the two-pore device can detect purine vs. pyrimidine homopolymeric segments within the ssDNA.

Stochastic detangling of 7 kb ssDNA through a 10 nm pore in a 20 nm SiN membrane can be carried out as shown in Stefan et al., *Nano Lett.*, 10:1414-20, 2010. While the single-nanopore method in Stefan et al. 2010 unravels the ssDNA by the mechanical contact force between the tangled ssDNA and the pore/membrane surface, it is contemplated that the dual-pore competing voltage setup can electrophoretically force ssDNA to detangle near and in between the pores at sufficiently high competing voltages, by the action of each voltage force on the DNA backbone nearest each pore.

Detangling and subsequently precision control of the rate of ssDNA through the two pore setup is important for eventual sequencing of long ssDNA molecules. At sufficiently high voltage (~400 mV), it is possible to discriminate purine and pyrimidine homopolymeric segments within ss-DNA (Skinner et al., *Nano Lett.*, 9(8):2953-60, January 2009), which is valuable for diagnostic applications and possibly cancer research.

This example also explores the use of RecA, or perhaps other Single Strand DNA Binding (SSB) proteins, as detectable "speed-bumps" that are differentiable from the ssDNA ionic current by binding to the ssDNA and creating a larger impedance. These speed bumps will allow direct quantification of the controlled ssDNA speeds that are possible, which in turn will demonstrate that the required 1 ms/nt is achievable. Since RecA is not required to bind to specific trinucleotide sequence sites, but binds preferentially to TGG-repeating sequences and also tends to bind where RecA filaments are already formed, calibration experiments will require the use of other ssDNA binding molecules that do bind to specific known sequence locations. Having known binding sites that are detectable as they pass through each pore is required to determine the speed of the molecule as a function of the competing voltage values. A non-limiting example is to use duplex strands (or bead-tethered duplex strands) that hybridize to one or more known sites, from which the shifts in current could be used to detect passage of each duplex through each pore, and then estimate the passing strand speed for the chosen voltage values. Subsequently, RecA filaments can be formed and detected on such molecules, keeping the duplex feature(s) as benchmark detection points relative to which RecA filaments can be detected and their position inferred.

Methods for determining genetic haplotypes and DNA mapping by incorporating fluorescent labels into dsDNA (Xiao, et al., U.S. Pat. No. 7,771,944 B2, 2010) can also use the two pore device, since the bead labels (e.g., quantum dots, or any fluorescent label) is bulkier and will produce shifts in the current just as binding proteins on dsDNA would. Moreover, the two-pore method is simpler and much less expensive than using high resolution imaging methods (i.e., total internal reflection fluorescence microscopy) to detect and map the label positions. It is also noted that any velocity fluctuations caused by Brownian motion during controlled delivery are much less deleterious for detecting larger features (proteins, duplex segments, bead attachments) than for detecting smaller features.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

The invention claimed is:

1. A dual-pore, dual-amplifier device for simultaneously controlling the movement of a charged polymer through a first and a second pore, comprising:
   an upper chamber, a middle chamber and a lower chamber, wherein the upper chamber is in communication with the middle chamber through the first pore, and the middle chamber is in communication with the lower chamber through the second pore, wherein the device further comprises a power supply configured to provide a first voltage between the upper chamber and the middle chamber, and provide a second voltage between the middle chamber and the lower chamber, each voltage being independently adjustable, and wherein the device provides dual-amplifier electronics configured for independent voltage control and current measurement at each pore, wherein the two voltages are different in magnitude, and wherein the first and second pores are configured so that the charged polymer is capable of simultaneously moving across both pores in either direction and in a controlled manner,
   wherein the first pore and second pore are about 10 nm to about 100 nm apart from each other.

2. The device of claim 1, wherein the first and second pores are substantially coaxial.

3. The device of claim 1, wherein the device comprises a material selected from the group consisting of silicon, silicon nitride, silicon dioxide, graphene, carbon nanotubes, TiO2, HfO2, Al2O3, metallic layers, glass, biological nanopores, membranes with biological pore inserts, and combinations thereof.

4. The device of claim 1, wherein the first pore has a depth of at least about 0.3 nm separating the upper chamber and the middle chamber and the second pore has a depth of at least about 0.3 nm separating the middle chamber and the lower chamber.

5. The device of claim 1, wherein said first and said second voltages are configured to be independently clamped by said dual-amplifier electronics.

6. The device of claim 1, wherein the middle chamber is connected to a common ground relative to the two voltages.

7. The device of claim 1, wherein the middle chamber comprises a medium for providing conductance between each of the pores and the electrode in the middle chamber.

8. A method for controlling the movement of a charged polymer through a pore, comprising: providing the device of claim 1, and performing the following steps:
   (a) loading a sample comprising a charged polymer in one of the upper chamber, middle chamber or lower chamber of the device of claim 1, wherein the device is connected to a voltage-clamp or patch-clamp system for providing a first voltage between the upper chamber and the middle chamber, and a second voltage between the middle chamber and the lower chamber;
   (b) setting an initial first voltage and an initial second voltage so that the polymer moves between the chambers, thereby locating the polymer across both the first and second pores; and
   (c) adjusting the first voltage and the second voltage so that both voltages generate force to pull the charged polymer away from the middle chamber, wherein the two voltages are different in magnitude, under controlled conditions, so that the charged polymer moves across both pores in one direction and in a controlled manner.

9. The method of claim 8, wherein the sample is loaded into the upper chamber and the initial first voltage is set to pull the charged polymer from the upper chamber to the middle chamber and the initial second voltage is set to pull the polymer from the middle chamber to the lower chamber.

10. The method of claim 8, wherein the sample is loaded into the middle chamber and the initial first voltage is set to pull the charged polymer from the middle chamber to the upper chamber and the initial second voltage is set to pull the charged polymer from the middle chamber to the lower chamber.

11. The method of claim 8 wherein the charged polymer is a polynucleotide or a polypeptide.

12. The method of claim 11, wherein the polynucleotide is selected from the group consisting of a double-stranded DNA, single-stranded DNA, double-stranded RNA, single-stranded RNA, and DNA-RNA hybrid.

13. The method of claim 8 wherein the adjusted first voltage and second voltage at step (c) are about 10 times to about 10,000 times as high, in magnitude, as the difference between the two voltages.

14. The method of claim 8 further comprising identifying a monomer unit of the polymer by measuring an ionic current across one of the pores when the monomer unit passes that pore.

15. The method of claim 14, wherein the monomer unit is a nucleotide.

16. The method of claim 14, wherein the monomer unit is a nucleotide pair.

17. The method of claim 13 wherein the monomer is bound to a molecule.

18. The method of claim 17, wherein the molecule is a DNA-binding protein or a nano-particle.

19. The method of claim 18, where the DNA-binding protein is a sequence-specific DNA-binding protein.

20. The method of claim 8 wherein the polymer is attached to a solid support at one end of the polymer.

21. A method for determining the sequence of a polynucleotide, comprising providing the device of claim 1, and performing the following steps:
(a) loading a sample comprising a polynucleotide in the upper chamber of the device of claim 1, wherein the device is connected to a voltage-clamp or patch-clamp system for providing a first voltage between the upper chamber and the middle chamber, and a second voltage between the middle chamber and the lower chamber, wherein the polynucleotide is optionally attached to a solid support at one end of the polynucleotide;
(b) setting an initial first voltage and an initial second voltage so that the polynucleotide moves from the upper chamber to the middle chamber and from the middle chamber to the lower chamber, thereby locating the polymer across both the first and second pores;
(c) adjusting the first voltage and the second voltage so that both voltages generate force to pull the polynucleotide away from the middle chamber, wherein the two voltages are different in magnitude, under controlled conditions, so that the polynucleotide moves across both pores in one direction and in a controlled manner; and
(d) identifying each nucleotide of the polynucleotide that passes through one of the pores, by measuring an ionic current across the pore when the nucleotide passes that pore.

22. The device of claim 1, wherein the first pore and the second pore are about 1 nm to about 100 nm in diameter.

23. The device of claim 1 wherein the first pore and second pore are about 1 nm to about 100 nm in diameter, and about 10 nm to about 1000 nm apart from each other.

24. The device of claim 1 wherein the first pore and the second pore are about 10 nm to about 500 nm apart from each other.

25. The device of claim 1, further comprising a charged polymer, wherein the charged polymer extends through both the first and second pores at the same time.

26. The device of claim 1, wherein the first voltage and second voltage are about 10 times to about 10,000 times as high, in magnitude, as the difference between the two voltages.

27. The device of claim 1, wherein each of the chambers comprise an electrode for connecting to a power supply and wherein a net voltage differential between the first and second voltages is present across the upper and lower chambers.

28. The device of claim 1, wherein the movement, and the rate of movement of the charged polymer is controllable by the relative magnitude and direction of the voltages.

29. The device of claim 1 wherein the first pore and the second pore are about 0.3 nm to about 100 nm in depth.

* * * * *

UNITED STATES PATENT AND TRADEMARK OFFICE
CERTIFICATE OF CORRECTION

| | |
|---|---|
| PATENT NO. | : 8,961,763 B2 |
| APPLICATION NO. | : 13/882191 |
| DATED | : February 24, 2015 |
| INVENTOR(S) | : William Dunbar et al. |

Page 1 of 1

It is certified that error appears in the above-identified patent and that said Letters Patent is hereby corrected as shown below:

In the claims,

Col. 20, line 14, In claim 1, please replace "100 nm" with "1000 nm."

Signed and Sealed this
Twentieth Day of October, 2015

Michelle K. Lee
*Director of the United States Patent and Trademark Office*